(12) United States Patent
Farascioni et al.

(10) Patent No.: US 8,444,038 B2
(45) Date of Patent: May 21, 2013

(54) TISSUE STOP FOR SURGICAL INSTRUMENT

(75) Inventors: David Farascioni, Bethel, CT (US); Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 267 days.

(21) Appl. No.: 12/899,954

(22) Filed: Oct. 7, 2010

(65) Prior Publication Data

US 2012/0080473 A1  Apr. 5, 2012

Related U.S. Application Data

(60) Provisional application No. 61/388,650, filed on Oct. 1, 2010.

(51) Int. Cl.
*A61B 17/04* (2006.01)

(52) U.S. Cl.
USPC .................. 227/178.1; 227/19; 227/175.1

(58) Field of Classification Search
USPC ...................... 227/178.1, 175.1, 19
See application file for complete search history.

(56) References Cited

U.S. PATENT DOCUMENTS

| | | |
|---|---|---|
| 3,017,637 A | 1/1962 | Sampson |
| 3,079,606 A | 3/1963 | Bobrov et al |
| 3,499,591 A | 3/1970 | Green |
| 4,576,167 A | 3/1986 | Noiles |
| 4,633,874 A | 1/1987 | Chow et al. |
| 4,664,305 A | 5/1987 | Blake, III et al. |
| 4,715,520 A | 12/1987 | Roehr, Jr. et al. |
| 4,819,853 A | 4/1989 | Green |
| 4,881,544 A | 11/1989 | Green et al. |
| 4,924,864 A | 5/1990 | Danzig |
| 5,014,899 A | 5/1991 | Presty et al. |
| 5,071,430 A | 12/1991 | De Salis et al. |
| 5,104,025 A | 4/1992 | Main et al. |
| 5,156,315 A | 10/1992 | Green et al. |
| 5,180,092 A | 1/1993 | Crainich |
| 5,307,976 A | 5/1994 | Olson et al. |
| 5,318,221 A | 6/1994 | Green et al. |
| 5,358,506 A | 10/1994 | Green et al. |
| 5,366,477 A | 11/1994 | LeMarie, III et al. |
| 5,379,933 A | 1/1995 | Green et al. |

(Continued)

FOREIGN PATENT DOCUMENTS

EP  0 600 182  6/1994

OTHER PUBLICATIONS

European Search Report for EP 11250468.3 dated Aug. 10, 2011.
European Search Report for EP 11178544 dated Sep. 29, 2011.

*Primary Examiner* — Brian D Nash

(57) ABSTRACT

A surgical instrument including a handle assembly, an elongate portion, a pair of opposed jaw members and a tissue stop is disclosed. The elongate portion extends distally from the handle assembly, and the pair of opposed jaw members extend distally from the elongate portion. The pair of opposed jaw members include first and second jaw members. The tissue stop cammingly engaged with the first jaw member and is movable between a first position where at least a portion of a stopping portion of the tissue stop is disposed between a tissue-contacting surface of the first jaw member and a tissue-contacting surface of the second jaw member and a second position where the portion of the stopping portion is between the tissue-contacting surface of the first jaw member and a lower surface of the first jaw member.

11 Claims, 11 Drawing Sheets

U.S. PATENT DOCUMENTS

| | | | |
|---|---|---|---|
| 5,389,098 | A | 2/1995 | Tsuruta et al. |
| 5,397,324 | A | 3/1995 | Carroll et al. |
| 5,403,312 | A | 4/1995 | Yates et al. |
| 5,413,268 | A | 5/1995 | Green et al. |
| 5,415,334 | A | 5/1995 | Williamson, IV et al. |
| 5,423,471 | A | 6/1995 | Mastri et al. |
| 5,452,837 | A | 9/1995 | Williamson, IV et al. |
| 5,465,895 | A | 11/1995 | Knodel et al. |
| 5,470,008 | A | 11/1995 | Rodak |
| 5,484,451 | A | 1/1996 | Akopov et al. |
| 5,487,500 | A | 1/1996 | Knodel et al. |
| 5,551,622 | A | 9/1996 | Yoon |
| 5,562,241 | A | 10/1996 | Knodel et al. |
| 5,597,107 | A | 1/1997 | Knodel et al. |
| 5,601,573 | A | 2/1997 | Fogelberg et al. |
| 5,634,584 | A | 6/1997 | Okorocha et al. |
| 5,651,491 | A | 7/1997 | Heaton et al. |
| 5,653,373 | A | 8/1997 | Green et al. |
| 5,655,698 | A | 8/1997 | Yoon |
| 5,662,258 | A | 9/1997 | Knodel et al. |
| 5,662,259 | A | 9/1997 | Yoon |
| 5,662,260 | A | 9/1997 | Yoon |
| 5,673,841 | A | 10/1997 | Schulze et al. |
| 5,680,982 | A | 10/1997 | Schulze et al. |
| 5,681,330 | A | 10/1997 | Hughett et al. |
| 5,762,255 | A * | 6/1998 | Chrisman et al. .......... 227/175.2 |
| 5,794,834 | A | 8/1998 | Hamblin et al. |
| 5,800,449 | A | 9/1998 | Wales |
| 5,816,471 | A | 10/1998 | Plyley et al. |
| 5,911,352 | A | 6/1999 | Racenet et al. |
| 5,984,938 | A | 11/1999 | Yoon |
| 5,988,479 | A | 11/1999 | Palmer |
| 5,993,465 | A | 11/1999 | Shipp et al. |
| 6,010,054 | A | 1/2000 | Johnson et al. |
| 6,050,472 | A | 4/2000 | Shibata |
| 6,119,913 | A | 9/2000 | Adams et al. |
| 6,131,789 | A | 10/2000 | Schulze et al. |
| 6,174,309 | B1 | 1/2001 | Wrublewski et al. |
| 6,241,140 | B1 | 6/2001 | Adams et al. |
| 6,601,749 | B2 | 8/2003 | Sullivan et al. |
| 6,607,540 | B1 | 8/2003 | Shipp |
| 6,755,338 | B2 | 6/2004 | Hahnen et al. |
| 6,805,273 | B2 | 10/2004 | Bilotti et al. |
| 6,978,921 | B2 | 12/2005 | Shelton, IV et al. |
| 6,988,650 | B2 | 1/2006 | Schwemberger et al. |
| 7,000,818 | B2 | 2/2006 | Shelton, IV et al. |
| 7,055,731 | B2 | 6/2006 | Shelton, IV et al. |
| 7,070,083 | B2 | 7/2006 | Jankowski |
| 7,134,587 | B2 | 11/2006 | Schwemberger et al. |
| 7,147,139 | B2 | 12/2006 | Schwemberger et al. |
| 7,147,140 | B2 | 12/2006 | Wukusick et al. |
| 7,204,404 | B2 | 4/2007 | Nguyen et al. |
| 7,207,472 | B2 | 4/2007 | Wukusick et al. |
| 7,210,609 | B2 | 5/2007 | Leiboff et al. |
| 7,278,563 | B1 | 10/2007 | Green |
| RE40,237 | E | 4/2008 | Bilotti |
| 7,380,696 | B2 | 6/2008 | Shelton, IV et al. |
| 7,407,078 | B2 | 8/2008 | Shelton, IV et al. |
| 7,434,717 | B2 | 10/2008 | Shelton, IV et al. |
| 7,451,904 | B2 | 11/2008 | Shelton, IV |
| 7,464,849 | B2 | 12/2008 | Shelton, IV et al. |
| 7,503,474 | B2 | 3/2009 | Hillstead et al. |
| 7,565,993 | B2 | 7/2009 | Milliman et al. |
| 7,568,604 | B2 | 8/2009 | Ehrenfels et al. |
| 7,896,214 | B2 * | 3/2011 | Farascioni ................. 227/180.1 |
| 2003/0229344 | A1 | 12/2003 | Dycus et al. |
| 2005/0139636 | A1 | 6/2005 | Schwemberger et al. |
| 2005/0145672 | A1 | 7/2005 | Schwemberger et al. |
| 2005/0247752 | A1 | 11/2005 | Kelly et al. |
| 2005/0247753 | A1 | 11/2005 | Kelly et al. |
| 2006/0144898 | A1 | 7/2006 | Bilotti et al. |
| 2007/0029364 | A1 | 2/2007 | Kruszynski et al. |
| 2007/0039995 | A1 | 2/2007 | Schwemberger et al. |
| 2007/0039996 | A1 | 2/2007 | Mather et al. |
| 2007/0039997 | A1 | 2/2007 | Mather et al. |
| 2007/0114261 | A1 | 5/2007 | Ortiz et al. |
| 2007/0175950 | A1 | 8/2007 | Shelton, IV et al. |
| 2007/0181631 | A1 | 8/2007 | Bilotti et al. |
| 2007/0187456 | A1 | 8/2007 | Viola et al. |
| 2007/0219563 | A1 | 9/2007 | Voegele |
| 2007/0221702 | A1 | 9/2007 | Kruszynski |
| 2007/0246508 | A1 | 10/2007 | Green |
| 2007/0255296 | A1 | 11/2007 | Sauer |
| 2008/0027466 | A1 | 1/2008 | Vitali et al. |
| 2008/0093415 | A1 | 4/2008 | Bilotti |
| 2008/0105730 | A1 | 5/2008 | Racenet et al. |
| 2008/0169328 | A1 | 7/2008 | Shelton |
| 2008/0169329 | A1 | 7/2008 | Shelton et al. |
| 2008/0169330 | A1 | 7/2008 | Shelton et al. |
| 2008/0169331 | A1 | 7/2008 | Shelton et al. |
| 2008/0169332 | A1 | 7/2008 | Shelton et al. |
| 2008/0169333 | A1 | 7/2008 | Shelton et al. |
| 2008/0272171 | A1 | 11/2008 | Viola |
| 2009/0134199 | A1 | 5/2009 | Heinrich et al. |
| 2009/0272784 | A1 | 11/2009 | Farascioni |
| 2010/0072257 | A1 * | 3/2010 | Farascioni ................. 227/180.1 |
| 2010/0072258 | A1 | 3/2010 | Farascioni et al. |
| 2010/0213238 | A1 | 8/2010 | Farascioni et al. |
| 2011/0264137 | A1 * | 10/2011 | Farascioni et al. ............ 606/205 |

\* cited by examiner

TISSUE STOP FOR SURGICAL INSTRUMENT

CROSS REFERENCE TO RELATED APPLICATIONS

This application claims priority to, and benefit of, U.S. Provisional Application Ser. No. 61/388,650, filed Oct. 1, 2010, the disclosure of which is hereby incorporated by reference in its entirety.

BACKGROUND

1. Technical Field

The present disclosure relates generally to surgical instruments and, more specifically, to surgical instruments for surgically joining tissue.

2. Background of Related Art

Surgical stapling instruments used for applying parallel rows of staples through compressed living tissue are well known in the art. These surgical instruments are commonly employed for closing tissue or organs prior to transaction or resection, for occluding organs in thoracic and abdominal procedures, and for fastening tissue in anastomoses.

Typically, such surgical stapling instruments include an anvil assembly, a cartridge assembly for supporting an array of surgical staples, an approximation mechanism for approximating the anvil and cartridge and anvil assemblies, and a firing mechanism for ejecting the surgical staples from the cartridge assembly.

In use, a surgeon generally initially approximates the anvil and cartridge members. Next, the surgeon can fire the instrument to place staples in tissue. Additionally, the surgeon may use the same instrument or a separate instrument to cut the tissue adjacent or between the row(s) of staples. In certain surgical stapling instruments, the instrument sequentially ejects the staples from the staple cartridge while the anvil and cartridge are approximated. The staples are driven through the tissue and formed against the anvil.

SUMMARY

The present disclosure relates to a surgical instrument for surgically joining tissue. The surgical instrument includes a handle assembly, an elongate portion, a pair of opposed jaw members and a tissue stop. The handle assembly includes a movable handle. The elongate portion extends distally from the handle assembly and defines a longitudinal axis. The pair of opposed jaw members are operatively coupled to the elongate portion and extend distally therefrom. The pair of opposed jaw members include a first jaw member and a second jaw member. The tissue stop is configured to retain the tissue between the pair of opposed jaw members. The tissue stop is connected with the first jaw member via a cam and is movable between a first position, where a stopping portion of the tissue stop is disposed between a tissue-contacting surface of the first jaw member and a tissue-contacting surface of the second jaw member, and a second position, where the stopping portion is between the tissue-contacting surface of the first jaw member and a lower surface of the first jaw member.

In various embodiments, the first jaw member includes a first camming slot on first lateral side thereof.

In various embodiments, the tissue stop includes at least one camming pin laterally extending from the first lateral side thereof. A first camming pin may be configured to slidably engage the first camming slot. The first camming slot may be disposed on a distal portion of the first jaw member.

In various embodiments, the first camming slot on the first jaw member is substantially parallel to the tissue-contacting surface of the first jaw member.

In various embodiments, the first camming slot on the first jaw member is curved with respect to the tissue-contacting surface of the first jaw member.

In certain embodiments, a second camming slot on the first jaw member is substantially parallel to the tissue-contacting surface of the first jaw member and disposed distal of the first camming slot.

In various embodiments, the stopping portion of the tissue stop is substantially orthogonal to the tissue-contacting surface of the first jaw member when the tissue stop is in the first position.

In various embodiments, the surgical instrument further includes a biasing member coupled to the tissue stop to urge the tissue stop toward its first position. The tissue stop may be configured to move toward its second position when the first jaw member is moved relative to the second jaw member. An upper surface of the tissue stop may be substantially flush with the tissue-contacting surface of the first jaw member when the tissue stop is in the second position.

The present disclosure also relates to a loading unit including a body portion, a pair of jaw members and a tissue stop. The body portion includes a proximal portion configured for releasable engagement with an elongate portion of the surgical instrument. The pair of jaw members extends distally from the body portion. At least one of the jaw members is movable with respect to the other between an open position and an approximated position engaging a body tissue therebetween. Moreover, the pair of jaw members includes a first jaw member and a second jaw member. The tissue stop is configured to retain the tissue between the pair of opposed jaw members. The tissue stop is connected with the first jaw member via a cam and is movable between a first position, where a stopping portion of the tissue stop is between a tissue contact surface of the first jaw member and a tissue contact surface of the second jaw member, and a second position, where the stopping portion is between the tissue-contacting surface of the first jaw member and a lower surface of the first jaw member.

In various embodiments, the first jaw member includes at least one camming slot on at least one lateral side thereof.

In various embodiments, the tissue stop includes at least one camming pin laterally extending from at least one lateral side thereof. The at least one camming pin may slidably engage with the at least one camming slot.

In various embodiments, the at least one camming slot is disposed on a distal portion of the first jaw member.

In various embodiments, the at least one camming slot on the first jaw member is substantially parallel to the tissue-contacting surface of the first jaw member.

In some embodiments, one of the at least one camming slot on the first jaw member is curved with respect to the tissue-contacting surface of the first jaw member. Another of the at least one camming slot on the first jaw member may be substantially parallel to the tissue-contacting surface of the first jaw member and may be disposed distal of the other camming slot.

In certain embodiments, the stopping portion of the tissue stop is substantially orthogonal to the tissue-contacting surface of the first jaw member when the tissue stop is in the first position.

In various embodiments, the surgical instrument further includes a biasing member coupled to the tissue stop to urge the tissue stop toward its first position. The tissue stop may be configured to move toward it second position when at least one jaw member is moved toward the other jaw member.

In various embodiments, an upper surface of the tissue stop is flush with the tissue-contacting surface of the first jaw member when the tissue stop is in the second position.

In another embodiment of the present disclosure a surgical instrument for surgically joining a tissue is disclosed. The surgical instrument includes a handle assembly, an elongate portion, a pair of opposed jaw members, and a tissue stop. The handle assembly includes a movable handle. The elongate portion extends distally from the handle assembly and defines a longitudinal axis. The pair of opposed jaw members are operatively coupled to the elongate portion and extend distally therefrom. The pair of opposed jaw members includes a first jaw member and a second jaw member. The tissue stop is mechanically engaged with the first jaw member and is configured to retain the tissue between the pair of opposed jaw members. The tissue stop is movable between a first position, where a stopping portion of the tissue stop is disposed between a tissue-contacting surface of the first jaw member and a tissue-contacting surface of the second jaw member, and a second position, where the stopping portion is between the tissue-contacting surface of the first jaw member and a lower surface of the first jaw member. A portion of the tissue stop is made of stamped metal section and a portion of the tissue stop is made of an overmolded plastic section.

In various embodiments, the stopping portion of the tissue stop includes a scalloped portion. In various embodiments, the scalloped portion of the tissue stop includes a plurality of spaced-apart semi-circular indents.

In various embodiments, the tissue stop includes a pair of lateral walls. In various embodiments, the stopping portion is disposed on a proximal edge of each lateral wall. In another embodiment of the present disclosure, a loading unit configured for releasable engagement with a surgical instrument is disclosed. The loading unit includes a body portion, a pair of jaw members, and a tissue stop. The body portion defines a longitudinal axis and includes a proximal portion configured for releasable engagement with an elongate portion of the surgical instrument. The pair of jaw members extends distally from the body portion. At least one of the jaw members is movable with respect to the other between an open position and an approximated position engaging a body tissue therebetween. The pair of jaw members includes a first jaw member and a second jaw member. The tissue stop is mechanically engaged with the first jaw member and is configured to retain the tissue between the pair of opposed jaw members. The tissue stop is movable between a first position, where a stopping portion of the tissue stop is disposed between a tissue-contacting surface of the first jaw member and a tissue-contacting surface of the second jaw member, and a second position, where the stopping portion is between the tissue-contacting surface of the first jaw member and a lower surface of the first jaw member. A portion of the tissue stop is made of stamped metal section and a portion of the tissue stop is made of an overmolded plastic section.

In various embodiments, the stopping portion of the tissue stop of the loading unit includes a scalloped portion. In various embodiments, the scalloped portion of the tissue stop includes a plurality of spaced-apart semi-circular indents.

In various embodiments, the tissue stop of the loading unit includes a pair of lateral walls. In various embodiments, the stopping portion is disposed on a proximal edge of each lateral wall. Another embodiment of the present disclosure relates to a tissue stop for use with a surgical instrument. The tissue stop includes a stamped metal portion and an overmolded plastic portion. The tissue stop is mechanically engaged with a jaw member of the surgical instrument and is configured to retain the tissue between opposed jaw members of the surgical instrument.

In various embodiments, the tissue stop includes a pair of lateral walls. In various embodiments, a stopping portion is disposed on a proximal edge of each lateral wall. In various embodiments, the stopping portion includes a scalloped portion. In various embodiments, the scalloped portion of the tissue stop includes a plurality of spaced-apart semi-circular indents.

BRIEF DESCRIPTION OF FIGURES

Various embodiments of the presently disclosed surgical instrument are disclosed herein with reference to the drawings, wherein.

DETAILED DESCRIPTION

Figure 1:
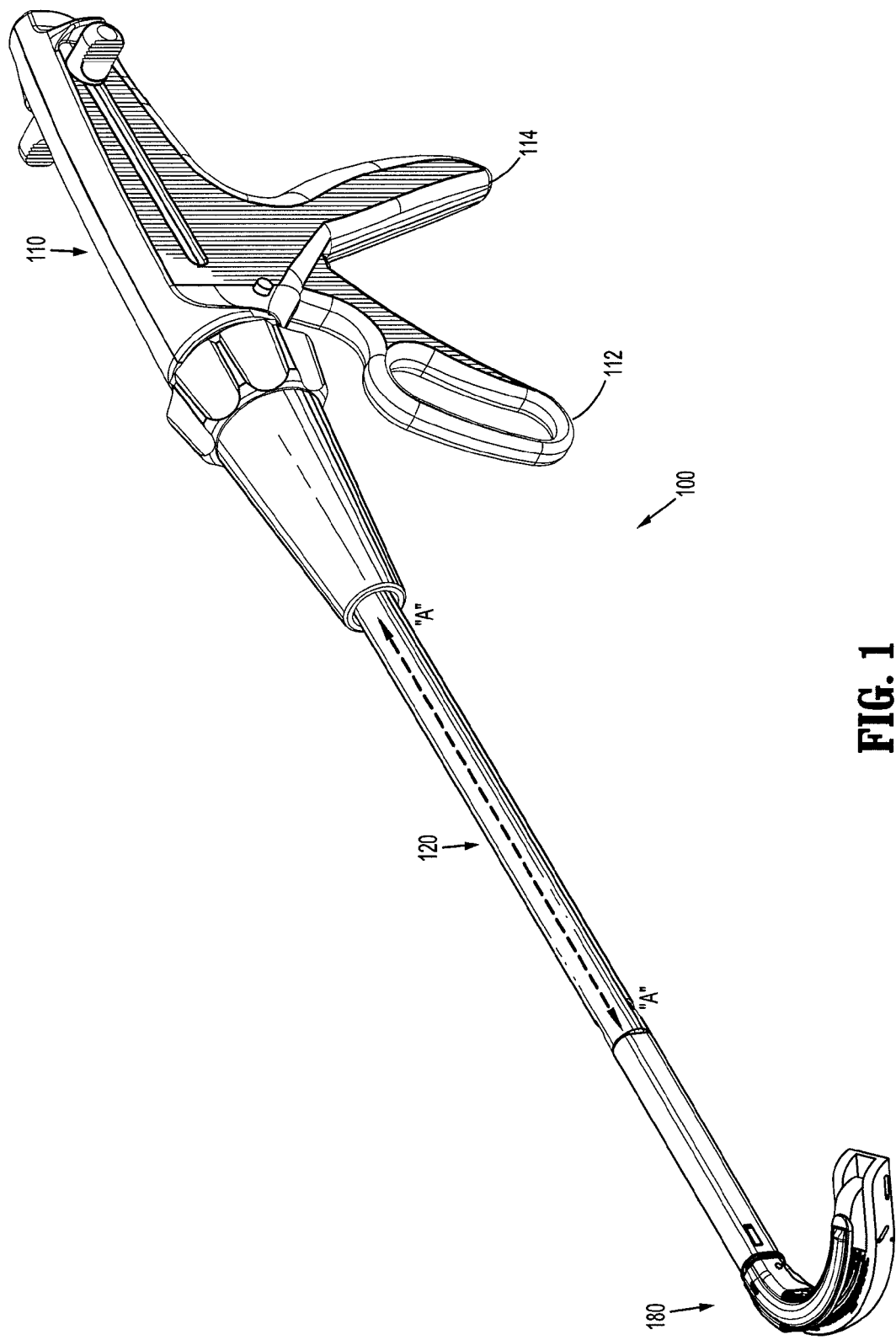
FIG. 1 is a perspective view of a surgical instrument in accordance with the present disclosure.

Embodiments of the presently disclosed surgical instrument are described in detail with reference to the drawings, wherein like reference numerals designate similar or identical elements in each of the several views. In the drawings and the description that follows, the term "proximal" refers to the end of the surgical instrument that is closest to the operator, whereas the term "distal" refers to the end of the surgical instrument that is farthest from the operator.

As appreciated by one skilled in the art, the depicted surgical instrument fires staples, but it may be adapted to fire any other suitable fastener such as clips and two-part fasteners. Additionally, the disclosed tissue stop may be used with an electrosurgical forceps. Further details of electrosurgical forceps are described in commonly-owned patent application Ser. No. 10/369,894, filed on Feb. 20, 2003, entitled VESSEL SEALER AND DIVIDER AND METHOD OF MANUFACTURING THE SAME, the entire contents of which are hereby incorporated by reference herein.

With reference to FIG. 1, reference numeral 100 designates an embodiment of the presently disclosed surgical instrument. In the interest of brevity, the present disclosure focuses on an end effector and a tissue stop of surgical instrument 100. U.S. Patent Applications Publication Nos. 2008/0105730, filed on Nov. 28, 2007; 2008/0110960, filed on Jan. 8, 2008; 2008/0142565, filed on Jan. 24, 2008; 2008/0041916, filed on Oct. 15, 2007; and Ser. No. 11/786,198, filed on Apr. 10, 2007, the disclosures of which are hereby incorporated by reference herein in their entirety, describe in detail the structure and operation of other surgical fastening assemblies.

Figure 2:
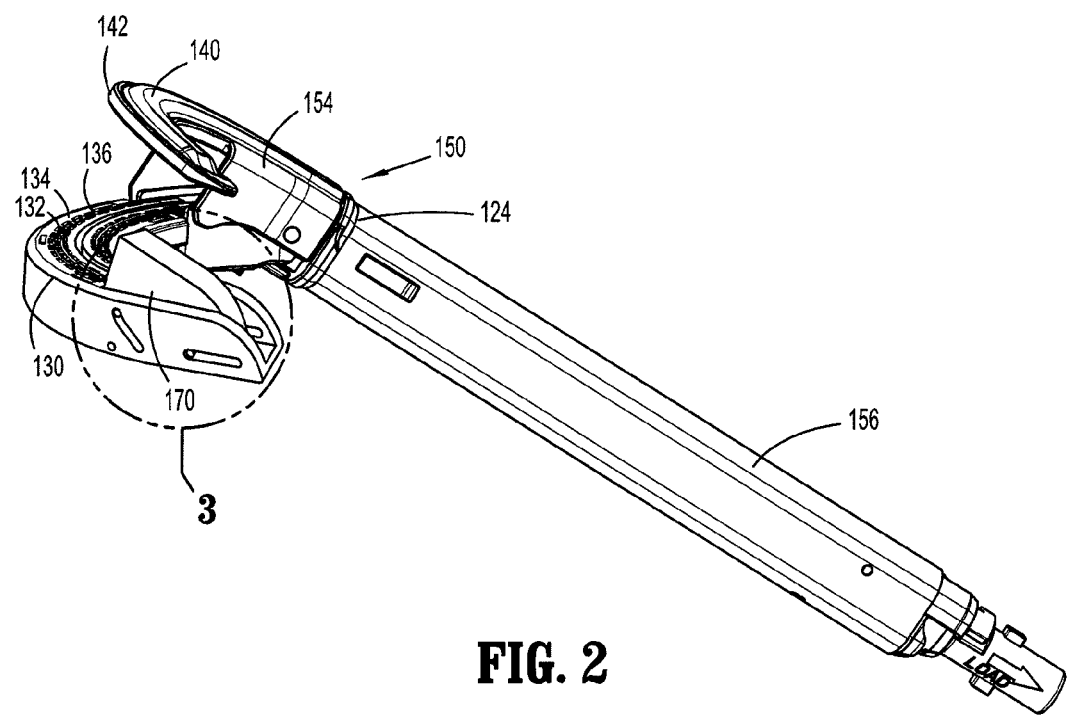
FIG. 2 is a perspective view of a loading unit of the surgical instrument of FIG. 1.

Surgical instrument 100 disclosed in the illustrated embodiments is configured to clamp, fasten, and/or cut tissue. In general, surgical instrument 100 includes a handle assembly 110, an elongate portion 120 extending distally from handle assembly 110 and defining a longitudinal axis "A-A," and a loading unit 180 (collectively referring to a single use loading unit ("SULU") and a disposable loading unit ("DLU")), as shown in FIG. 1. With reference to FIG. 2, loading unit 180 includes a proximal body portion 156, and a tool assembly 150. Proximal body portion 156 is configured to releasably attach to elongate portion 120 of surgical instrument 100 using a variety of attachment features, such as, for example, a bayonet coupling, latch, detent or snap-fit. In other embodiments, the instrument has jaws that are permanently attached to the elongate portion, and a replaceable cartridge, such as a staple cartridge, can be loaded, removed and reloaded in one of the jaws.

Tool assembly 150 includes end effector 154 and a tissue stop 170. End effector 154, which is disposed adjacent distal portion 124 of body portion 156, includes a first jaw member 130 and a second jaw member 140. As shown in FIGS. 1 and 2, each of first and second jaw members 130, 140 is longitudinally curved with respect to the longitudinal axis "A-A." The curved jaw members, as compared to straight jaw members, may help facilitate access to lower pelvic regions, e.g., during lower anterior resection ("LAR"). Additionally, the inclusion of curved jaw members may allow increased visualization to a surgical site and may also allow more room for a surgeon to manipulate target tissue or the jaw members themselves with his or her hand. While the illustrated embodiment depict the jaw members as being curved, it is envisioned and within the scope of the present disclosure that the tissue stop 170 may be used with linear jaw members.

At least one of the jaw members 130, 140 is adapted to move relative to the other jaw member (130 or 140) between spaced and approximated positions. In the illustrated embodiment, first jaw member 130 contains a cartridge assembly 132, and second jaw member 140 includes an anvil assembly 142. Cartridge assembly 132 moves with respect to anvil assembly 142 between spaced and approximated positions upon actuation of a movable handle 112, for example. While cartridge assembly 132 is shown as pivotally movable with respect to anvil assembly 142, anvil assembly 142 may be pivotally mounted with respect to the cartridge assembly 132.

Handle assembly 110 includes a stationary handle 114 and movable handle 112. Movable handle 112 is adapted to move pivotally towards or away from stationary handle 114. Further, movable handle 112 is operatively connected to anvil assembly 142 through a mechanism adapted to convert at least a partial actuation of movable handle 112 into a pivoting motion of at least one of cartridge assembly 132 and anvil assembly 142 between spaced and approximated positions. As recognized by one skilled in the art, any conventional actuation mechanism may be employed to operatively couple movable handle 112 to tool assembly 150.

With reference to FIG. 2, cartridge assembly 132 has a tissue-contacting surface 134 and a plurality of fastener retaining slots 136. Tissue-contacting surface 134 generally faces anvil assembly 142 and, during operation, engages tissue when the anvil assembly 142 is approximated with cartridge assembly 132. Fastener retaining slots 136 are arranged in rows along tissue contacting surface 134 and each fastener retaining slot 136 is adapted to releasably hold a fastener (not shown). For example, when movable handle 112 is pivoted toward stationary handle 114, the fasteners are ejected from fastener retaining slots 136 and move towards anvil assembly 142.

Cartridge assembly 132 also includes a knife channel 138 (FIG. 3) adapted to slidably receive a knife (not shown) or any other suitable cutting tool. Knife channel 138 is defined in the staple cartridge, is disposed between rows of fastener retaining slots 136, and extends along tissue-contacting surface 134. In operation, the knife slides through the knife channel 138 when movable handle 112 pivots towards stationary handle 114. Alternatively, other mechanisms can be used to drive the knife through knife channel 138.

In disclosed embodiments, handle assembly 110 contains an actuation mechanism for deploying the fasteners from fastener retaining slots 136 and advancing a knife along knife channel 138. This actuation mechanism includes a firing rod (not shown) operatively connected to movable handle 112. In operation, pivoting movable handle 112 toward stationary handle 114 causes firing rod to advance distally. Firing rod is in turn operatively coupled to an axial drive assembly at least partially positioned within tool assembly 150. Axial drive assembly is configured to move distally in response to a distal translation of firing rod. The axial drive assembly includes a drive beam that incorporates the knife, an upper member, and a lower member. As the upper member of the drive beam engages the anvil assembly and the lower member of the drive beam engages the cartridge assembly, the distal translation of axial drive assembly causes the anvil assembly 142 to pivot toward the cartridge assembly 132. In addition, the axial drive assembly pushes an actuation sled disposed within the cartridge assembly 132 in a distal direction, while the actuation sled translates distally through end effector 154. As the actuation sled advances distally through the cartridge assembly 132, this actuation sled urges the fasteners out of the fastener retaining slots 136. In certain embodiments, axial drive assembly includes a knife or blade mounted on a distal portion thereof. In operation, the drive beam, including the knife, moves through the knife channel 138 when axial drive assembly moves distally through end effector 154. Further details of an endoscopic surgical stapling instrument are described in detail in commonly-owned U.S. Pat. No. 6,953,139 to Milliman et al., the entire contents of which are hereby incorporated by reference herein. However, it is also envisioned that other methods of approximating the jaw members are also usable, including sliding a clamp bar (not shown). Other methods of ejecting the fasteners are contemplated, such as cam bars, are contemplated.

Figure 3:
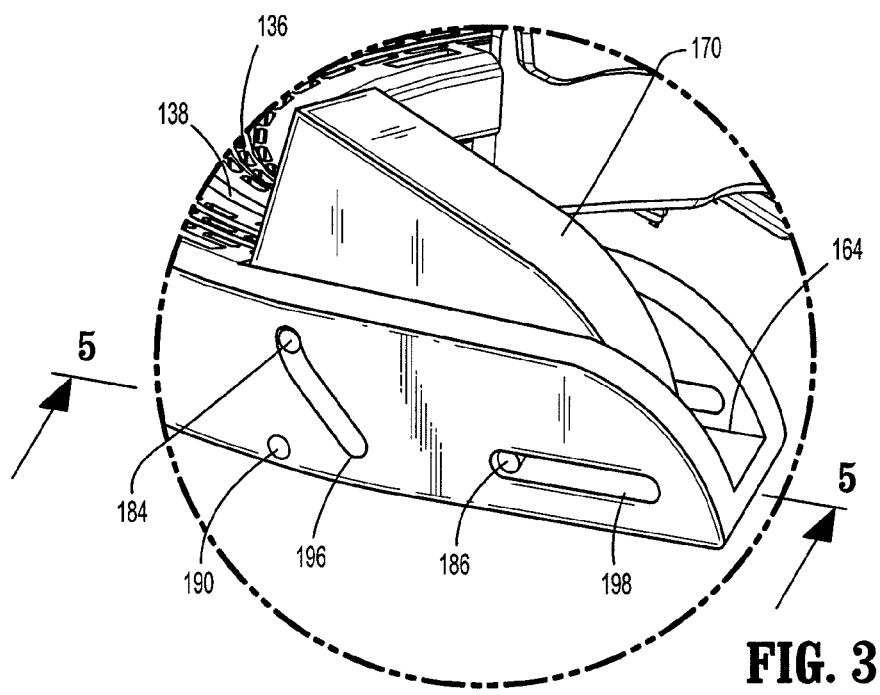
FIG. 3 is a perspective view of the area of detail of FIG. 2 illustrating a tissue stop.
Figure 4:
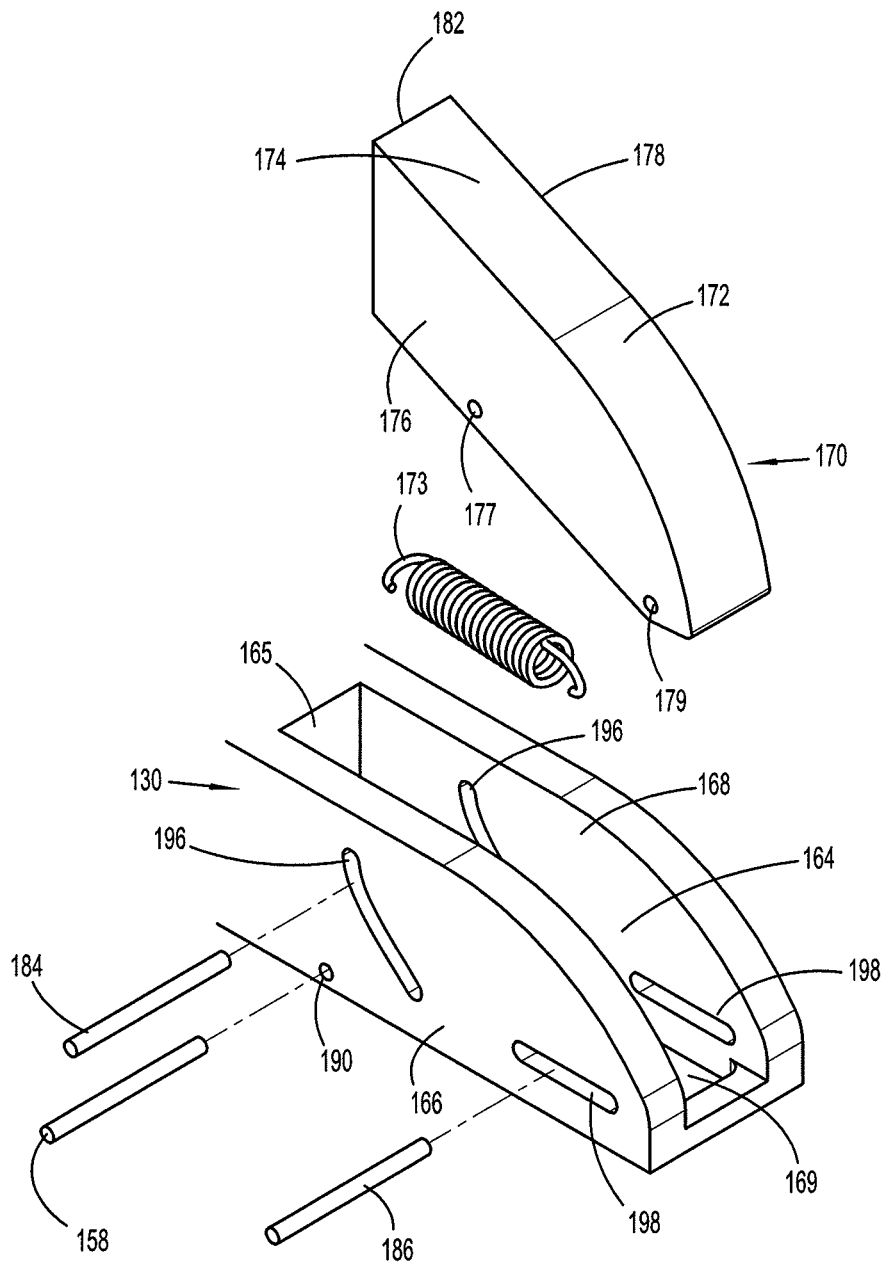
FIG. 4 is a perspective exploded view of a distal portion of a jaw member of the surgical instrument including the tissue stop of FIG. 3.

With reference to FIGS. 3 and 4, tissue stop 170 is movably disposed at least partially within a recess 164 defined in a distal portion of jaw member 130. The term "distal" typically refers to that part or component of the instrument that is farther away from the user. As used herein, the terms "distal" and "proximal" will take into account the curvature of curved parts of the surgical instrument of the present disclosure. For example, "distal" will refer to the portion of the curved part that is farthest from the user, along a trajectory defined by the curved part. That is, while an intermediate portion of a curved part may be farther from the user during use, the portion of the curved part that is farthest along its longitudinal axis is considered "distal."

The distal portion of jaw member 130 defines recess 164 and includes a proximal wall 165, a pair of side walls 166, 168 and a lower surface 169. Tissue stop 170 includes a body 172 having an upper, tissue-contacting surface 174, a pair of lateral walls 176, 178, and a stopping portion 182 configured and adapted to engage tissue (e.g., tissue that is distally directed from between the jaw members).

A pair of camming pins, including a proximal camming pin 184 and a distal camming pin 186, is also disclosed. Each camming pin 184, 186 is configured to extend transversely through both lateral walls 176, 178 of body 172. Proximal camming pin 184 is configured to extend through a first pair of holes 177 of body 172 (only a single hole 177 is shown on lateral wall 176; the hole that is disposed through lateral wall 178 is not visible in FIG. 4), and is configured to engage a pair of proximal cam slots 196, which extend at least partially through each side wall 166, 168 of recess 164. Distal camming pin 186 is configured extend through a second pair of holes 179 of body 172 (only a single hole 179 is shown on lateral wall 176; the hole that is disposed through lateral wall 178 is not visible in FIG. 4), and is configured to engage a pair of distal cam slots 198, which extend at least partially through each side wall 166, 168 of recess 164. As can be appreciated, the engagement between camming pins 184, 186, jaw member 130, and tissue stop 170 movably secure tissue stop 170 to jaw member 130.

In the illustrated embodiments, distal cam slots 198 are substantially parallel to tissue-contacting surface 134 of jaw member 130, and proximal cam slots 196 form an angle with respect to tissue-contacting surface 134 of jaw member 130. It is envisioned that proximal cam slots 196 include at least one curved portion, at least one linear portion, or combinations of at least one curved and at least one linear portion. The illustrated configuration of cam slots 196, 198 allows tissue stopping portion 182 to be movable in and out of recess 164 adjacent proximal wall 165 with a reduced clearance gap "G" therebetween (see FIG. 5). It is also envisioned that gap "G" may be minimized at every moment when tissue stop 170 moves from the first position to the second position. Other cam arrangements can be used to connect the tissue stop to the jaw. The cam can be shaped to maximize the height of the tissue stop when the tissue stop is extended from the jaw (the first position) and/or minimize the space within the jaw occupied by the tissue stop when the tissue stop is in the retracted, second position.

Figure 5:
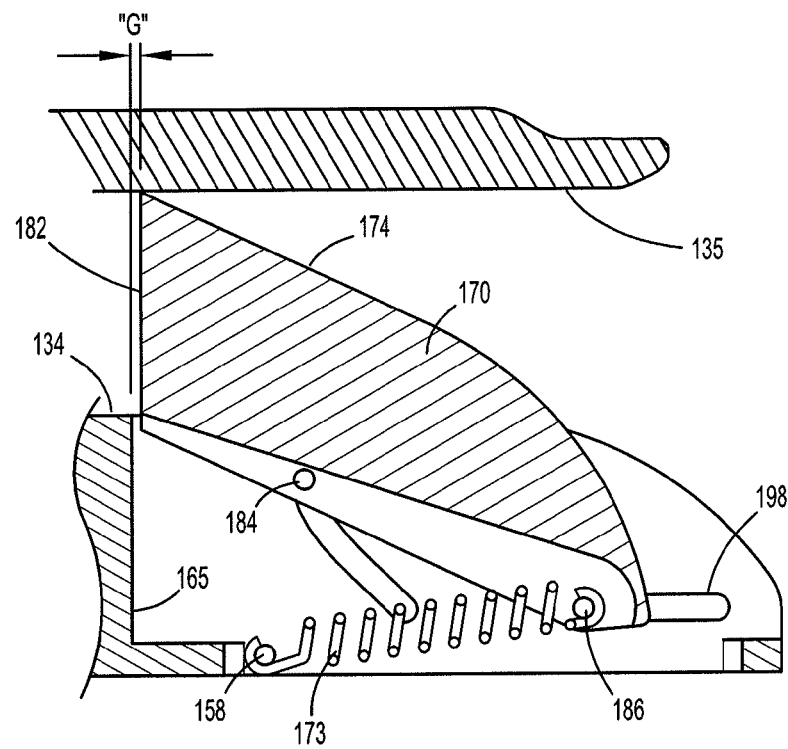
FIG. 5 is a longitudinal cross-sectional view of the tissue stop mechanically engaged with the jaw members of the surgical instrument.

As shown in FIG. 5, tissue stop 170 also includes a biasing member 173. Biasing member 173 is configured to mechanically engage camming pin 186 and to mechanically engage a support pin 158 that extends through an opening 190 (see FIG. 4) on each side wall 166, 168 of jaw member 130. However, it is also contemplated that any other retaining member, such as, for example, a post, may replace support pin 158 to retain one end of biasing member 173. Biasing member 173 urges distal camming pin 186 to its proximal-most position within camming slots 198. In response to the distal camming pin 186 being proximally urged, proximal camming pin 184 is also proximally urged due to the mechanical relationship between camming pins 184, 186, biasing member 173, and tissue stop 170. When camming pins 184, 186 are in their proximal-most positions within camming slots 196, 198, respectively, tissue stop 170 is located in a first position, in which stopping portion 182 is exposed and extends at least partially out of recess 164, i.e., disposed between tissue-contacting surfaces 134, 135 of cartridge and anvil assemblies 132, 142, respectively (see FIG. 5, for example).

Figure 8:
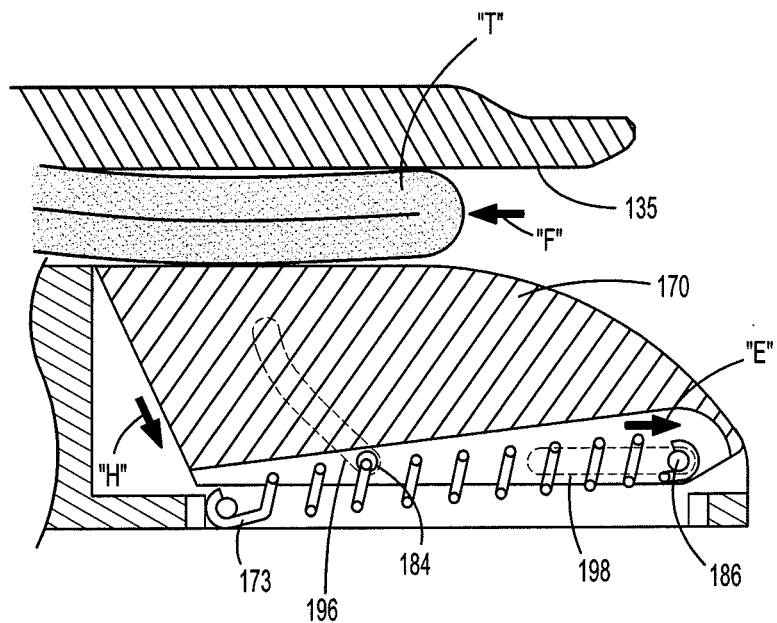

Tissue stop 170 is movable between the first position, as shown in FIG. 5, and a second position, as illustrated in FIG. 8. In the first position which corresponds to when jaw members 130, 140 are in an open position, at least a portion (e.g., a majority, or the entire portion) of stopping portion 182 is exposed out of recess 164. The approximation of the jaw members 130, 140 causes tissue stop 170 to move towards its second position. That is, as one jaw member (e.g., jaw member 140) moves towards the other jaw member (e.g., jaw member 130), tissue-contacting surface 135 contacts tissue-contacting surface 174 of tissue stop 170, and physically urges tissue stop 170 towards its second position against the bias of biasing member 173. In the second position which corresponds to when jaw members 130, 140 are in the approximated position, a majority (e.g., the entirety) of stopping portion 182 is disposed within recess 164. In this embodiment, when tissue stop 170 is disposed in the first position, stopping portion 182 is orthogonally disposed (e.g., substantially perpendicular) relative to tissue-contacting surface 134. As can be appreciated, such an orientation may help impede tissue from distally escaping tool assembly 150. In other embodiments, the instrument can include an actuator that is connected to the tissue stop so that the user can move the tissue stop between the first and second positions by manipulating a button or lever. Such actuator may also include a lock and/or latch for locking the position of the tissue stop.

Figure 6:
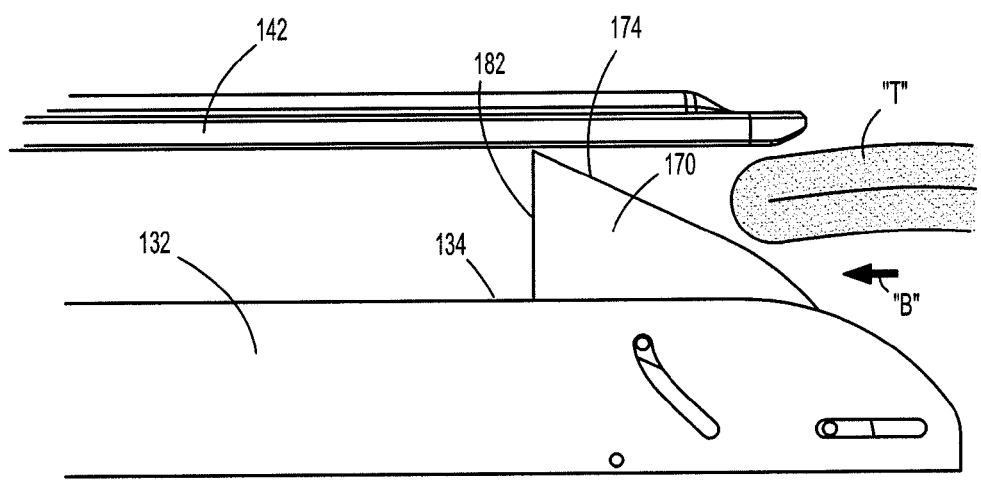
FIG. 6 is a side view of a portion of the jaw members and the tissue stop prior to insertion of tissue.
Figure 7:
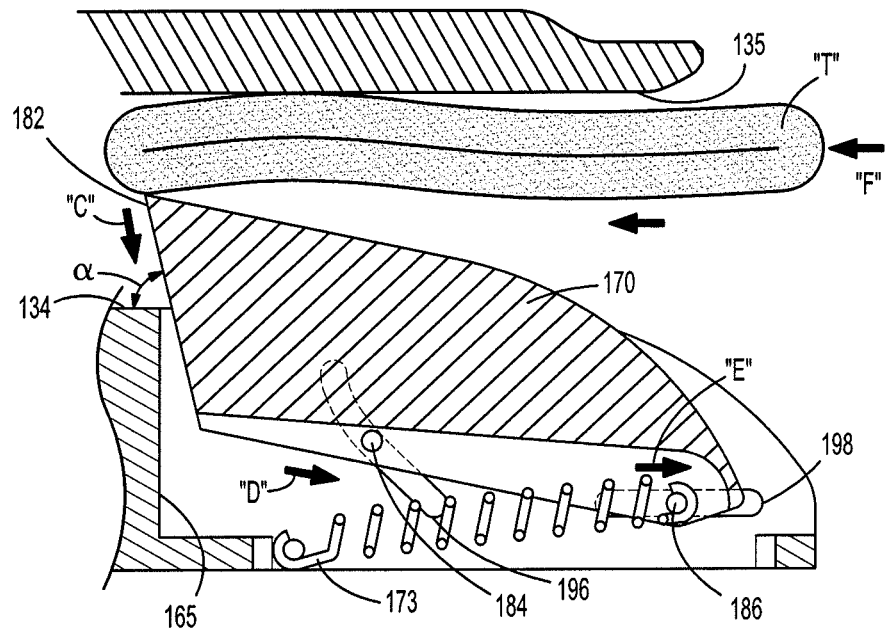
FIGS. 7-9 are longitudinal cross-sectional views of a portion of jaw members and a tissue stop interacting with the tissue at various stages of operation in accordance with another embodiment of the present disclosure.

In use, a surgeon initially positions surgical stapling instrument 100 adjacent a target tissue as shown in FIG. 6. Here, tissue stop 170 is in the first position where the jaw members 130, 140 are in an open position and at least a portion of stopping portion 182 is exposed out of recess 164. Then tissue "T" is introduced into tool assembly 150, between jaw members 130, 140. The angle defined by upper tissue-contacting surface 174 of tissue stop 170 facilitates introduction of tissue "T" into tool assembly 150 in the general direction of arrow "B," as seen in FIG. 6. As tissue "T" is proximally inserted into tool assembly 150, tissue "T" comes into contact with tissue stop 170 and may force at least a portion of stopping portion 182 into recess 164 in the general direction of arrow "C" as shown in FIG. 7. In certain embodiments, the tissue stop has a sloped surface facing the open end of the jaws to encourage the tissue to move the tissue stop. Alternatively, tissue "T" may be proximally inserted between the jaw members 130, 140 by moving in the space between the tissue-contacting surface 135 of jaw member 140 and tissue-contacting surface 174 of tissue stop 170 without necessarily contacting stop member 170.

When moved towards its second position, tissue stopping portion 182 moves in the general direction of arrow "C" (FIG. 7). As tissue stopping portion 182 is translated in the general direction of arrow "C," distal camming pin 186 distally translates along distal camming slot 198 in the general direction of arrow "E" (FIG. 7), while proximal camming pin 184 slides distally along proximal camming slot 184 in the general direction of arrow "D" (FIG. 7).

Figure 9:
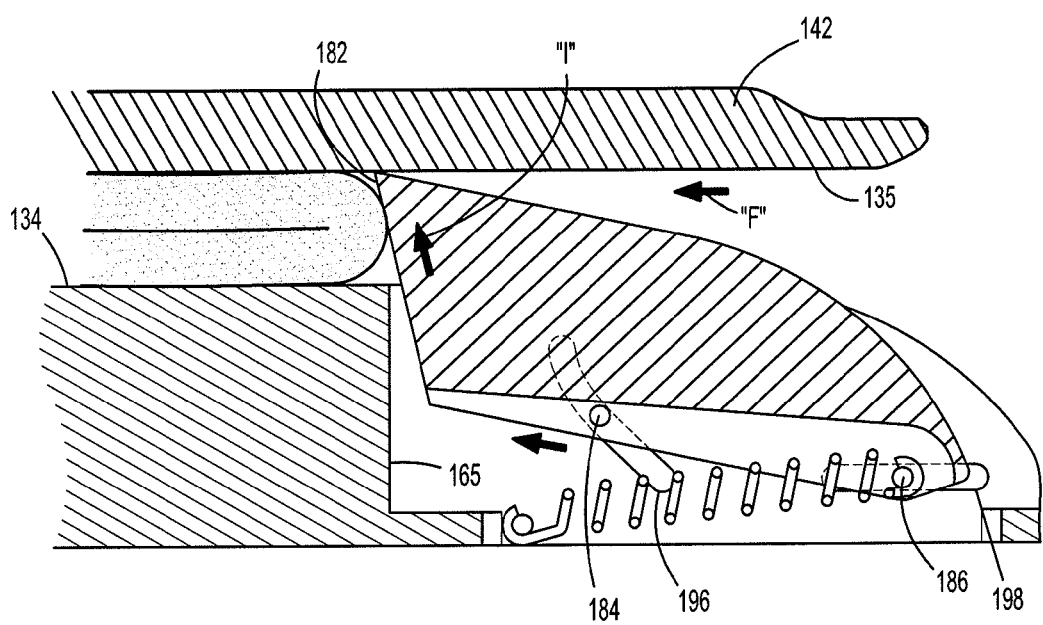

After the surgeon has placed at least a portion of tissue "T" between jaw members 130, 140, the surgeon can actuate an approximation mechanism, e.g., by pivoting movable handle 112 towards stationary handle 114 to approximate anvil assembly 142 towards cartridge assembly 132, to capture tissue "T" between tissue-contacting surfaces 134, 135 as shown in FIG. 8. Here, a proximal portion of tissue-contacting surface 174 of tissue stop 170 is substantially flush with tissue-contacting surface 134 of cartridge assembly 132, and anvil assembly 142 exerts a force against stop member 170 (through tissue "T") toward recess 164. In response to the force exerted by the anvil assembly 142 on tissue stop 170, camming pin 186 translates farther distally along camming slot 198 in the general direction of arrow "E" until the camming pin 186 is in the distal-most portion of camming slot 198. Additionally, camming pin 184 slides farther distally along camming slot 196 in the general direction of arrow "H" (FIG. 8) until camming pin 184 reaches the distal-most portion of camming slot 196, against the bias of biasing member 173. Tissue "T" is now interposed between jaw members 130, 140 and may be pushed farther proximally by surgeon in the general direction of arrow "F" (FIGS. 7-9). As a distal end of tissue "T" is pushed proximally of tissue stop 170 in the general direction of "F," the biasing force exerted by biasing member 173 pushes tissue stop 170 in the general direction of arrow "I," towards (and possibly against) tissue-contacting surface 135 of anvil assembly 142. Here, camming pins 184, 186 have moved proximally along camming slots 196, 198, respectively, proportional to the thickness of tissue "T."

In the embodiment illustrated in FIG. 9, tissue stop 170 is in contact with tissue-contacting surface 135 and is located distally of tissue "T," thereby impeding or preventing any distal escape of tissue "T." At this time, the surgeon may perform a surgical procedure on tissue "T," e.g., staple, seal and/or cut tissue "T." After performing the surgical procedure, jaw member 140 is moved away from jaw member 130, and tissue stop 170 returns to its first position in response to the biasing force.

Figure 10:
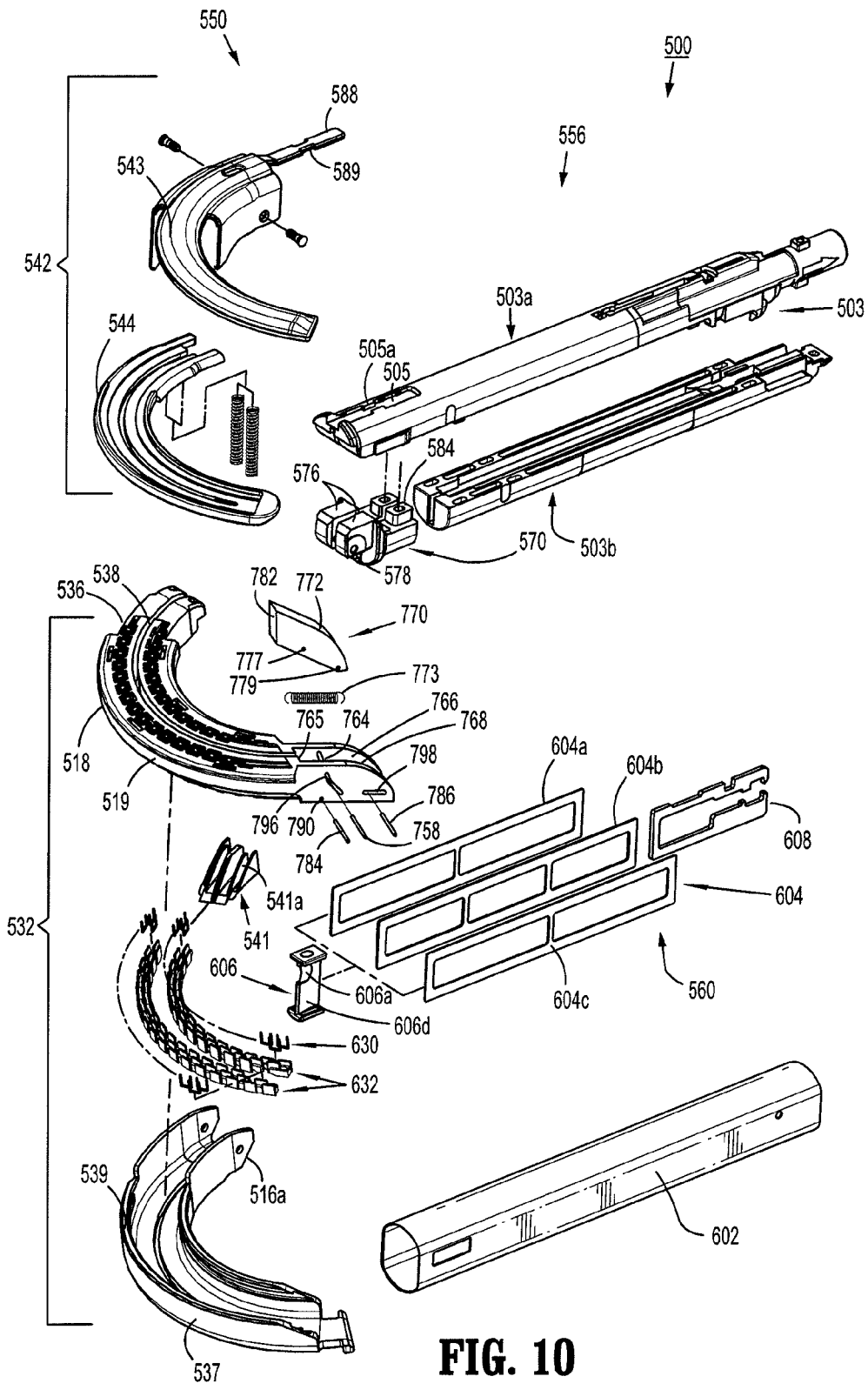
FIG. 10 is a perspective assembly view of a loading unit in accordance with another embodiment of the present disclosure.

With reference to FIG. 10, a loading unit 500 in accordance with another embodiment of the present disclosure is illustrated. Loading unit 500 includes a proximal body portion 556 and a tool assembly 550. Proximal body potion 556 is releasably attachable to a distal end of elongate portion 120. Tool assembly 550 includes a pair of jaw members including an anvil assembly 542 and a cartridge assembly 532. In particular, cartridge assembly 532 is pivotal in relation to anvil assembly and is movable between an open or unclamped position and a closed or approximated position.

Anvil assembly 542 includes a longitudinally curved anvil cover 543 and a longitudinally curved anvil plate 544, which defines a plurality of staple forming depressions. When tool assembly 550 is in the approximated position, staple forming depressions are positioned in juxtaposed alignment with cartridge assembly 532. Cartridge assembly 532 includes a longitudinally curved carrier 537, which receives a longitudinally curved cartridge 518 via, for example, a snap-fit connection. Cartridge 518 includes a pair of support struts 519 which rest on sidewalls 539 of carrier 537 to stabilize cartridge 518 on carrier 537. An external surface of carrier 537 includes an angled cam surface 516a.

Cartridge 518 defines a plurality of laterally spaced staple retention slots 536. Each slot 536 is configured to receive a staple 630 therein. Cartridge 518 includes a central longitudinally curved slot 538. As an actuation sled 541 moves through cartridge 518, cam wedges 541a of actuation sled 541 sequentially engage pushers 632 to move pushers 632 vertically within staple retention slots 536 and eject staples 630 into staple forming depressions of anvil plate 544. Subsequent to the ejection of staples 630 from retention slots 536, a cutting edge 606a of dynamic clamping member 606 severs the stapled tissue as cutting edge 606a travels through curved slot 538 of cartridge 518.

With continued reference to FIG. 10, proximal body portion 556 includes an inner body 503 formed from molded half-sections 503a and 503b and a drive assembly 560. Proximal body portion 556 is coupled to tool assembly 550 by a mounting assembly 570. Mounting assembly 570 has a pair of extensions 576 which extend into a proximal end of carrier 537. Each extension 576 has a transverse bore 578 which is aligned with holes 516A of carrier 539 such that mounting assembly 570 is pivotally secured to cartridge 518 with carrier 539. Mounting assembly 570 is fixedly secured to half-section 503a by a pair of vertical protrusions 584. Vertical protrusions 584 extend upwardly from mounting assembly 570 and frictionally fit into corresponding recesses in half-section 503a.

Anvil cover 543 includes a proximally extending finger 588 having a pair of cutouts 589 formed therein. Cutouts 589 are positioned on each lateral side of finger 588 to help secure anvil cover to half-section 503a. Half-section 503a includes a channel 505 that includes a pair of protrusions 505a. Finger 588 of anvil cover mechanically engages channel 505 of half-section 503a, such that cutouts 589 are aligned with protrusions 505a. An outer sleeve 602 covers the finger 588 and channel 505. The configuration of finger 588 and channel 505 facilitates a secure connection between anvil cover 543 and half-section 503a. Moreover, this connection results in a non-movable (e.g., non-pivotable) anvil assembly 542 with respect to proximal body portion 556.

Drive assembly 560 includes a flexible drive beam 604 which is constructed from three stacked metallic sheets 604a-c and a proximal engagement portion 608. At least a portion of drive beam 604 is sufficiently flexible to be advanced through the curvature of the tool assembly 550. Drive beam 604 has a distal end which is secured to a dynamic clamping member 606. Dynamic clamping member 606 includes a knife or cutting edge 606a at a distal face of vertical strut 606d.

Loading unit 500 includes a tissue stop 770 movably disposed at least partially within a recess 764 defined in a distal portion of cartridge 518. Recess 764 is defined by a proximal wall 765, a pair of side walls 766, 768 and a lower surface. Tissue stop 770 includes a body 772 having an upper, tissue-contacting surface, a pair of lateral walls and a stopping portion 782 configured and adapted to engage tissue. A proximal camming pin 758 and a distal camming pin 786 are each configured to extend transversely through both lateral walls 766, 768 of body 772. Proximal camming pin 758 is configured to extend through a first through hole 777 of body 772, and is configured to engage a pair of proximal cam slots 796, which extend at least partially through each side wall 766, 768. Distal camming pin 786 is configured to extend through a second through hole 779 of body 772, and is configured to engage a pair of distal cam slots 798, which extend at least partially through each side wall 766, 768. It is also contemplated that at least one 796, 798 is only defined in one of the side walls 766, 768.

Tissue stop 770 also includes a biasing member 773. Biasing member 773 is configured to mechanically engage camming pin 786 and to mechanically engage a support pin 784 that extends through an opening 790 (see FIG. 4) on each side wall 766, 768 of cartridge assembly 532. Biasing member 773 urges distal camming pin 786 to its proximal-most position within camming slots 798. In response to the urging of distal camming pin 786 in the proximal direction, proximal camming pin 758 is also proximally urged due to the mechanical relationship between camming pins 758, 786, biasing member 773, and tissue stop 770. When camming pins 758, 786 are in their proximal-most positions within camming slots 796, 798, respectively, stopping portion 782 is exposed and extends at least partially out of recess 764. The operation of loading unit 500 is substantially similar to those described above and will be omitted in the interest of brevity.

Figure 11:
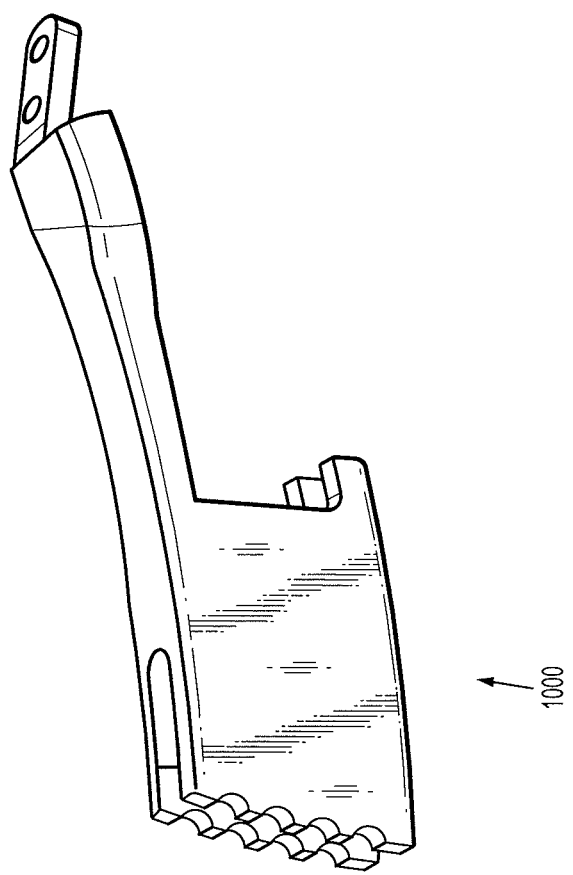
FIGS. 11 and 12 are perspective views of a tissue stop including a stamped metal portion and an overmolded plastic portion for use with the surgical instrument of FIG. 1 in accordance with an embodiment of the present disclosure.
Figure 12:
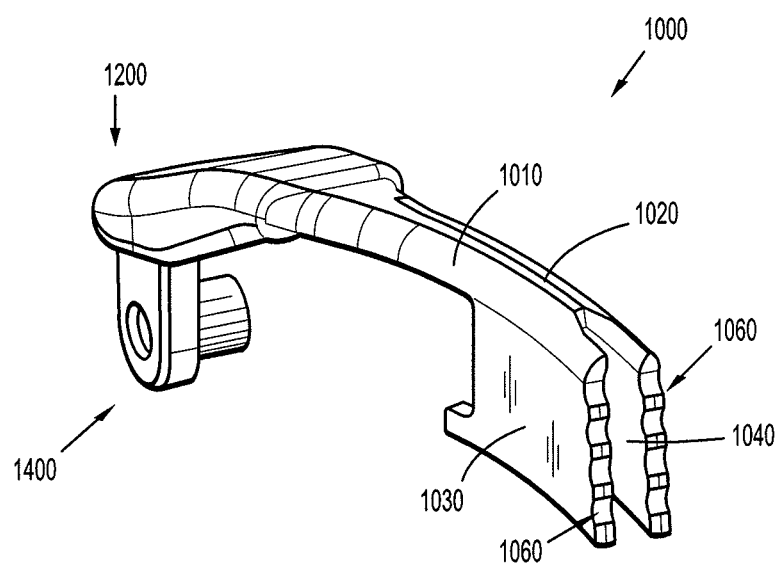
Figure 14:
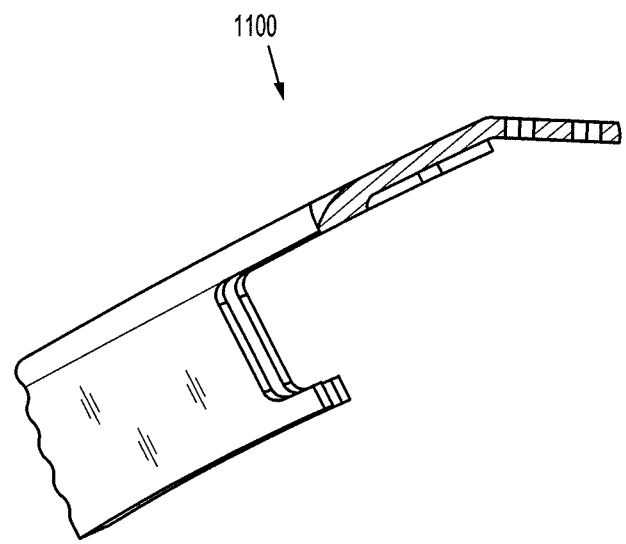
FIGS. 14-17 are various views of the stamped metal portion of the tissue stop of FIGS. 11 and 12.
Figure 13:
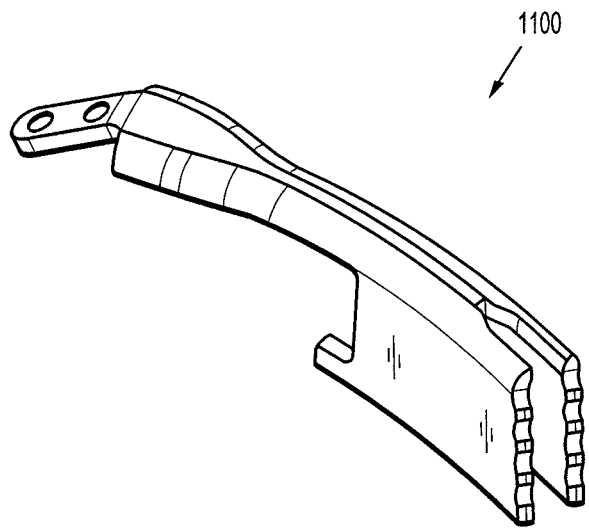
FIG. 13 is a perspective view of a stamped metal portion of the tissue stop of FIGS. 11 and 12.
Figure 15:
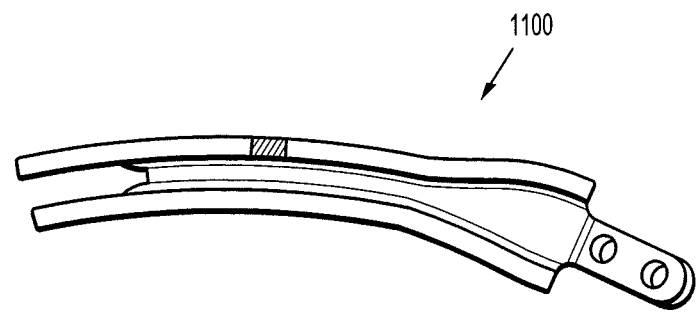
Figure 16:
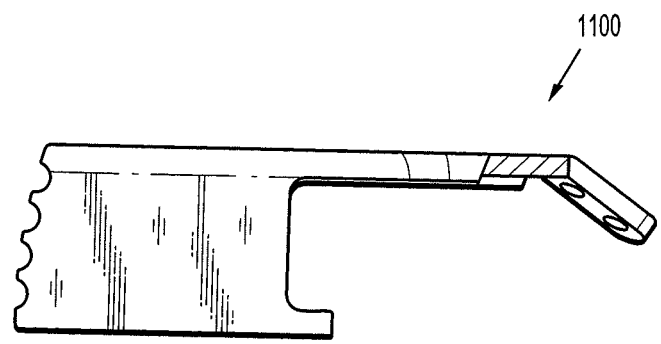
Figure 17:
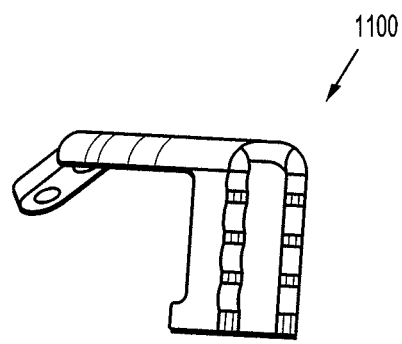

With reference to FIGS. 11-17, a tissue stop 1000 in accordance with an embodiment of the present disclosure is illustrated. Tissue stop 1000 is made of two parts: a stamped metal section 1100 and an overmolded plastic section 1200. The stamped metal section 1100 is illustrated in FIGS. 13-17, and the overmolded plastic section 1200, which at least partially covers the stamped metal section 1100, is illustrated in FIGS. 11-12. The multiple piece design of the tissue stop 1000 provides the strength of the metal while allowing complex geometries that are suitable for plastic injection molding. While particular portions of tissue stop 1000 are shown being made from stamped metal, it is envisioned and within the scope of the present disclosure that the stamped metal portion 1100 can include a greater or lesser portion of the entire tissue stop 1000. Likewise, the overmolded plastic section 1200 may also include a greater or lesser portion of the entire tissue stop 1000 than what is illustrated.

Tissue stop 1000 includes a body 1010 having an upper, tissue-contacting surface 1020, a pair of lateral walls 1030, 1040, and a stopping portion 1050 configured and adapted to engage tissue (e.g., tissue that is distally directed from between the jaw members). Stopping portion 1050 of tissue stop 1000 includes a scalloped portion 1060 including a plurality of spaced-apart semi-circular indents. More specifically, scalloped portion 1060 is disposed on a proximal edge of each lateral wall 1030, 1040. As can be appreciated, scalloped portion 1060 is configured to help prevent tissue from sliding with respect to tissue stop 1000.

Tissue stop 1000 is usable with the camming pins 184, 186, as discussed above with reference to tissue stop 170, and tissue stop 1000 may also include a pivoting protrusion 1400 extending transversely from body 1010, as shown in FIGS. 11 and 12. Pivoting protrusion 1400 is configured to pivotably engage a portion of the cartridge assembly to enable pivotal movement therebetween.

Additionally, in disclosed embodiments, the surgical instrument 100 and loading unit 180 described in connection with FIGS. 1 through 10 includes the stamped/molded tissue stop 1000.

It will be understood that various modifications may be made to the embodiments of the presently disclosed surgical instruments. Therefore, the above description should not be construed as limiting, but merely as exemplifications of embodiments. Those skilled in the art will envision other modifications within the scope and spirit of the present disclosure.

What is claimed is:

1. A surgical instrument for surgically joining a tissue, the surgical instrument comprising:
    a handle assembly including a movable handle;
    an elongate portion extending distally from the handle assembly and defining a longitudinal axis;
    a pair of opposed jaw members operatively coupled to the elongate portion and extending distally therefrom, the pair of opposed jaw members including a first jaw member and a second jaw member, the first jaw member defining first and second cam slots; and
    a tissue stop configured to retain the tissue between the pair of opposed jaw members, the tissue stop being operatively coupled to the first jaw member, the tissue stop including a pair of cams slidably engaging the first and second cam slots, respectively, the tissue stop being movable between a first position, where a stopping portion of the tissue stop is disposed between a tissue-contacting surface of the first jaw member and a tissue-contacting surface of the second jaw member, and a second position, where the stopping portion is disposed between the tissue-contacting surface of the first jaw member and a lower surface of the first jaw member, wherein the first and second cam slots define an obtuse angle therebetween.

2. The surgical instrument of claim 1, wherein the first-jaw first cam slot is disposed on a first lateral side the first jaw member.

3. The surgical instrument of claim 2, wherein the pair of cams laterally extends from a lateral side of the tissue stop.

4. The surgical instrument of claim 2, wherein the first cam slot is disposed on a distal portion of the first jaw member.

5. The surgical instrument of claim 1, wherein the stopping portion of the tissue stop is substantially orthogonal to the tissue-contacting surface of the first jaw member when the tissue stop is in the first position.

6. The surgical instrument of claim 1, further including a biasing member coupled to the tissue stop to urge the tissue stop toward its first position.

7. The surgical instrument of claim 6, wherein the tissue stop is configured to move toward its second position when the first jaw member is moved relative to the second jaw member.

8. The surgical instrument of claim 1, wherein an upper surface of the tissue stop is substantially flush with the tissue-contacting surface of the first jaw member when the tissue stop is in the second position.

9. The surgical instrument of claim 1, wherein one of the first and second cam slots is substantially linear to provide bi-directional translation of one of the pair of cams therein.

10. The surgical instrument of claim 9, wherein the other of the first and second cam slots defines a substantially non-linear curve.

11. The surgical instrument of claim 10, wherein the one of the first and second cam slots is distal of the other of the first and second cam slots.

* * * * *